United States Patent [19]
Euteneuer

[11] Patent Number: 5,499,980
[45] Date of Patent: Mar. 19, 1996

[54] POLYIMIDE BALLOON CATHETER AND METHOD OF MAKING SAME

[75] Inventor: Charles L. Euteneuer, St. Michael, Minn.

[73] Assignee: SciMed Life Systems, Inc., Maple Grove, Minn.

[21] Appl. No.: 260,683

[22] Filed: Jun. 16, 1994

Related U.S. Application Data

[63] Continuation of Ser. No. 101,349, Aug. 2, 1993, abandoned, which is a continuation of Ser. No. 847,799, Mar. 6, 1992, abandoned, which is a division of Ser. No. 798,851, Nov. 18, 1991, Pat. No. 5,207,700, which is a continuation of Ser. No. 617,430, Nov. 26, 1990, abandoned, which is a continuation of Ser. No. 364,116, Jun. 12, 1989, abandoned, which is a division of Ser. No. 229,313, Aug. 8, 1988, Pat. No. 4,952,357.

[51] Int. Cl.$^6$ .................................................. A61M 25/10
[52] U.S. Cl. .................. 606/28; 606/194; 604/96; 264/129; 264/255; 264/317; 264/305
[58] Field of Search .................. 604/96–103; 606/194, 606/192, 28, 7, 27; 264/129, 255, 305, 317, 573; 607/96, 113

[56] References Cited

U.S. PATENT DOCUMENTS

| | | | |
|---|---|---|---|
| 2,690,595 | 1/1954 | Raiche | 18/58.7 |
| 3,304,353 | 2/1967 | Harautuneian | 264/98 |
| 4,327,736 | 5/1982 | Inoue | 128/349 |
| 4,380,237 | 4/1983 | Newbower . | |
| 4,413,989 | 11/1983 | Schjeldahl et al. | 604/96 |
| 4,490,421 | 12/1984 | Levy | 428/35 |
| 4,497,074 | 2/1985 | Rey et al. | 3/1 |
| 4,547,193 | 10/1985 | Rydell | 604/282 |
| 4,552,127 | 11/1985 | Schiff . | |
| 4,641,649 | 2/1987 | Walinsky et al. . | |
| 4,643,186 | 2/1987 | Rosen et al. . | |
| 4,654,024 | 5/1987 | Crittenden et al. . | |
| 4,672,962 | 6/1987 | Hershenson . | |
| 4,695,697 | 9/1987 | Kosa | 219/121 LZ |
| 4,709,698 | 12/1987 | Johnston et al. . | |
| 4,737,219 | 4/1988 | Taller | 156/215 |
| 4,754,752 | 7/1988 | Ginsburg et al. . | |
| 4,790,311 | 12/1988 | Ruiz . | |
| 4,793,350 | 12/1988 | Mar et al. | 128/344 |
| 4,799,479 | 1/1989 | Spears . | |
| 4,807,620 | 2/1989 | Strul et al. . | |
| 4,808,164 | 2/1989 | Hess . | |
| 4,878,492 | 11/1989 | Sinofsky et al. | 606/16 |
| 4,976,720 | 12/1990 | Machold et al. | 606/194 |

FOREIGN PATENT DOCUMENTS

| | | |
|---|---|---|
| 1324241 | 12/1961 | France . |
| 773971 | 5/1957 | United Kingdom . |
| 2130093 | 5/1984 | United Kingdom . |

OTHER PUBLICATIONS

N. A. Adrova, et al., "Polyimides, A New Class of Heat-Resistant Polymers", pp. 4–13, (1969).

D. Adams, "Technical Notes: PTCA Balloon Materials, Their Characteristics, and Impact on Catheter Selection", (1988).

Niemand advertisement, MD&DI, Jul. 1983, p. 68.

Hudson Wire Company literature "Miniature Thin Wall Tubing".

*Primary Examiner*—Michael H. Thaler
*Attorney, Agent, or Firm*—Kinney & Lange

[57] ABSTRACT

A thin wall balloon for a balloon catheter is formed by depositing a film (such as polyimide) over a substrate which has an exterior surface configuration corresponding to a desired shape of the balloon in an inflated (or deflated) condition. After the polyimide film is cured, the substrate is removed from within the polyimide film by chemically dissolving the substrate.

22 Claims, 4 Drawing Sheets

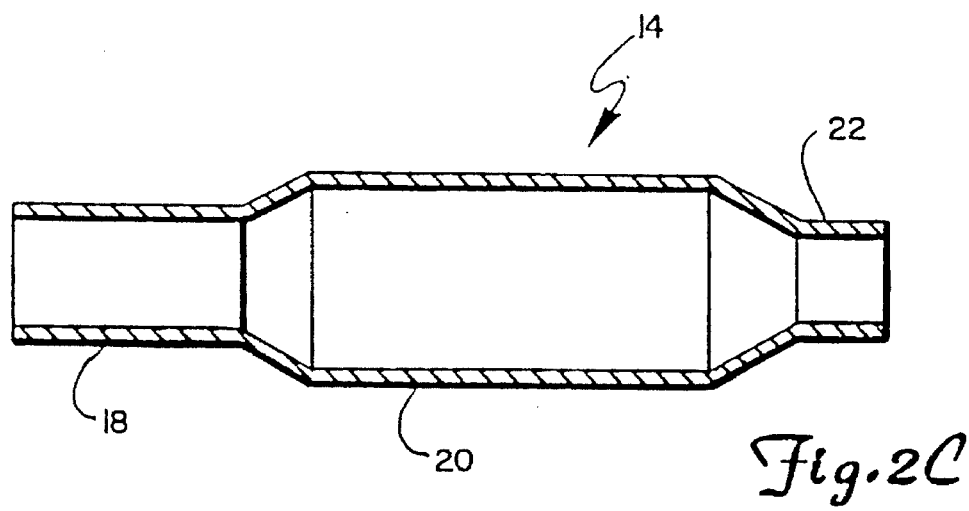
Fig. 2C
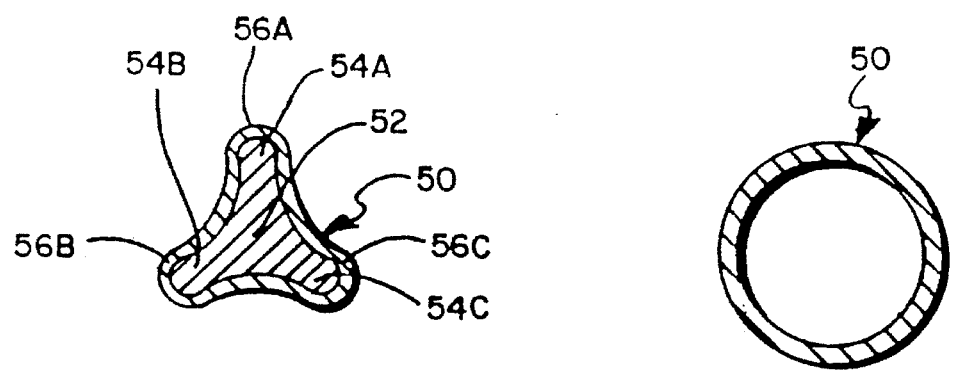
Fig. 3A
Fig. 3B

POLYIMIDE BALLOON CATHETER AND METHOD OF MAKING SAME

This is a continuation of application Ser. No. 08/101,349, filed Aug. 2, 1993, (now abandoned), which is a continuation of application Ser. No. 07/847,799, filed Mar. 6, 1992 (now abandoned), which is a division of application Ser. No. 07/798,851, filed Nov. 18, 1991, now issued as U.S. Pat. No. 5,207,700, which is a continuation of application Ser. No. 07/617,430, filed Nov. 26, 1990 (now abandoned), which is a continuation of application Ser. No. 07/364,116, filed Jun. 12, 1989 (now abandoned), which is a division of application Ser. No. 07/229,313, filed Aug. 8, 1988, now issued as U.S. Pat. No. 4,952,357.

BACKGROUND OF THE INVENTION

1. Field of the Invention

The present invention relates to balloon catheters useful in medical dilatation procedures.

2. Description of the Prior Art

Angioplasty has gained wide acceptance in recent years as a efficient and effective method for treating types of vascular diseases. In particular, angioplasty is widely used for opening stenoses in the coronary arteries, and is also used for treatment of stenoses in other parts of the vascular system.

The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying fluid under pressure through an inflation lumen to the balloon. The inflation of the balloon causes stretching of the artery and pressing of the lesion into the artery wall to reestablish acceptable blood flow through the artery.

In order to treat very tight stenosis with small openings, there has been a continuing effort to reduce the profile of the catheter so that the catheter not only can reach but also can cross such a very tight stenosis. An important factor in the profile of the dilatation catheter is the wall thickness of the balloon material.

Balloons for dilatation balloon catheters have been made from a wide variety of polymeric materials. Typically the balloon wall thicknesses have been on the order of 0.002 to 0.003 inches with most materials. There have been continuing efforts, however, to develop thin wall balloon materials which have much thinner walls than the standard wall thicknesses (and thus are capable of lower profile) while still having the necessary distensibility and burst pressure rating. One example of a thin wall balloon is described in the Levy U.S. Pat. No. 4,490,421. In the Levy patent, molded balloons made of a polyethylene terephthalate (PET) homopolyester are described. PET-balloons having wall thicknesses on the order of 0.0002 inches have been developed.

Despite the advantage of very thin walls, PET balloons have been found to have a number of significant disadvantages. First, PET balloons formed by blow molding can exhibit pinholes which can emit a high velocity jet of inflation fluid during inflation. This jet can cause artery dissection. Second, PET exhibits low tear resistance. Third, PET balloons will not distend more than about 5%, so that higher inflation pressures will not allow the physician to fully open a stenosis if the balloon proves to be slightly smaller than what is needed. Fourth, PET balloons are very susceptible to damage, and can not be touched. Fifth, PET will not take a crease (which is advantageous for folding the balloon).

There is a continuing need for improved balloon catheters and, in particular, for alternative thin wall balloon materials and fabrication methods.

SUMMARY OF THE INVENTION

A thin wall balloon for use in a balloon catheter is formed by depositing a film (preferably a polymer film such as polyimide) over the exterior surface of a substrate which has an exterior surface configuration corresponding to the desired shape of the balloon in a predetermined condition. The film is then cured, and the substrate is removed from within the film, leaving the finished balloon.

In one preferred embodiment of the present invention, the substrate is removed by chemically dissolving the substrate. The substrate is preferably a glass material, and an acid (such as HF) is used to attack and dissolve the glass material without affecting the film.

The balloon of the present invention features a very thin wall, with very close control over the inside diameter of the balloon and with wall thicknesses which are uniform throughout the balloon.

BRIEF DESCRIPTION OF THE DRAWINGS

FIGS. 2A–2C illustrate a preferred method of forming the dilatation balloon of the present invention.

FIGS. 3A and 3B illustrate a balloon formed in a normal deflated state and inflated in a pressurized state.

DETAILED DESCRIPTION OF THE PREFERRED EMBODIMENTS

Figure 1:
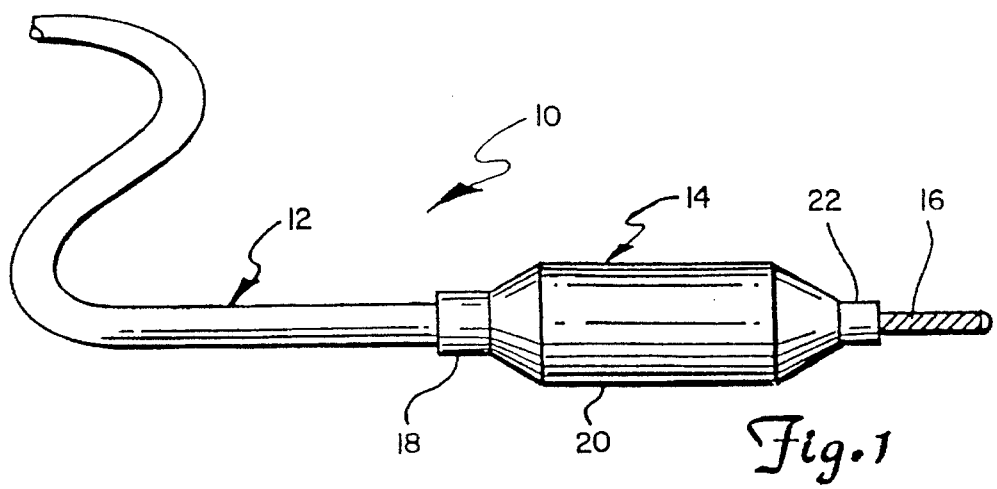
FIG. 1 is a perspective view of a balloon catheter using the balloon of the present invention.

FIG. 1 shows dilatation balloon catheter 10, which has an elongated flexible shaft 12 with inflatable thin wall balloon 14 mounted at its distal end. In FIG. 1, balloon 14 is shown in its fully inflated condition. Extending out the distal end of balloon 14 is flexible distal tip 16. Depending upon the particular construction of catheter 10, tip 16 may be the distal end of a movable guidewire which extends through shaft 12 and balloon 14, or may be the distal end of a fixed wire or core which is bonded to balloon 14.

Shaft 12, which is preferably a metal or polymeric tube, has at least one lumen extending from its proximal to its distal end. Depending upon the particular construction of catheter 10, multiple lumens may be provided in shaft 12. In any case, at least an inflation lumen extends through shaft 12 for selective inflation and deflation of balloon 14.

Balloon 14 is a thin wall balloon (preferably of a polymer material such as polyimide) which has a proximal waist portion 18 bonded to the distal end of shaft 12, an intermediate inflatable balloon section 20 of a larger diameter than waist section 18, and a smaller distal end section 22. The wall thickness of balloon 14 is less than about 0.001 inches, and is preferably on the order of about 0.0003 inches. This extremely thin wall characteristic provides a very low profile for balloon catheter 10.

Polyimide is a heterochain polymer made of two base monomers, a diamine and dianhydride (e.g. para-aminoanaline and pyromellitic dianhydride). Polyimide is typically formed by two step reaction like the following example. First, a polyamine is formed from the monomers. The reaction proceeds at about 25° C. and the product is soluble and stable in very polar solvents. Second, the polyamine is condensed to polyimide at about 120° C. to crosslink chain, drive off water and the remaining solvent. Further description of polyimides and their preparation can be found in Androva et al, *Polyimide, A New Class of Heat-Resistant Polymers*, pp 4–13, (1969), which is hereby incorporated by reference.

Figure 2A:
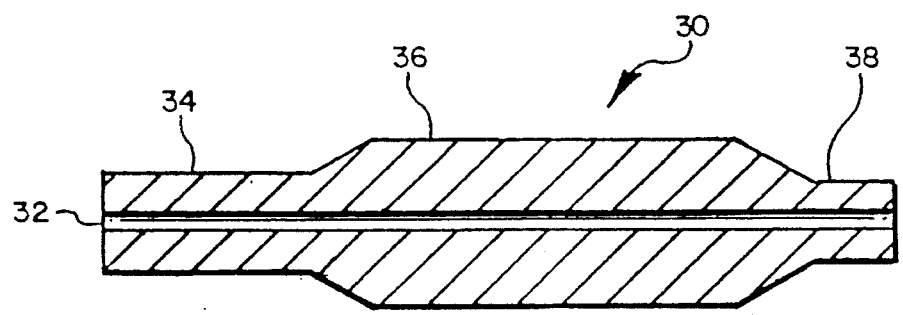
Figure 2B:
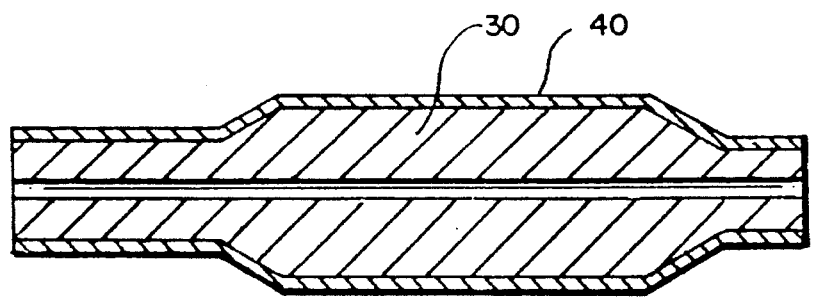

FIGS. 2A–2C illustrate the method of the present invention for forming polyimide balloon 14. As shown in FIG. 2A, substrate 30 is provided with an exterior surface of configuration which will determine the inner surface of balloon 14. This surface configuration corresponds to the desired interior surface configuration of balloon 14 when balloon 14 is fully inflated. In preferred embodiments of the present invention, substrate 30 is a material formed of a glass resin. As shown in FIG. 2A, substrate 30 has a central passage 32 extending axially through it, and has a proximal waist section 34, a balloon section 36 of greater outside diameter, and a distal tip section 38 of reduced outside diameter.

As shown in FIG. 2B, polyimide film 40 is deposited on the exterior surface of substrate 30. This step can be performed, for example, by dipping substrate 30 into thin polyamine solution and then heating substrate 30 and the deposited solution to form polyimide film 40. Each deposition formed with this technique is about 0.0001 inches thick. In preferred embodiments of the present invention, repeated dip coatings and heat curing is performed until the desired thickness of film 40 has been formed. In preferred embodiments, this thickness is on the order of about 0.0003 inches.

The next step in the process is the removal of substrate 30 from within the deposited polyimide film 40. Removal is preferably achieved by placing substrate 30 and film 40 into an HF acid bath to etch away glass substrate 30. Polyimide film 40 is not affected by the HF acid. FIG. 2C shows balloon 14 after substrate 30 has been completely removed.

The present invention has several important advantages. First, it offers extremely thin walls, and therefore is extremely well suited for low profile catheters. Second, the process of the present invention, as illustrated in FIGS. 2A–2C, offers close control over the inside diameter tolerances of balloon 14. Third, the method of the present invention, unlike other balloon fabrication techniques, yields a balloon having walls of uniform wall thickness throughout the entire balloon (i.e. waist 18, balloon 20 and distal section 22). Fourth, when polyimide is the polymer material deposited, the resulting balloon has the benefit of superior material properties compared to PET, such as higher tear resistance, greater strength and toughness, less susceptibility to damage, and the ability to take a crease (so that the balloon can be preformed to fold down when deflated).

Figure 4:
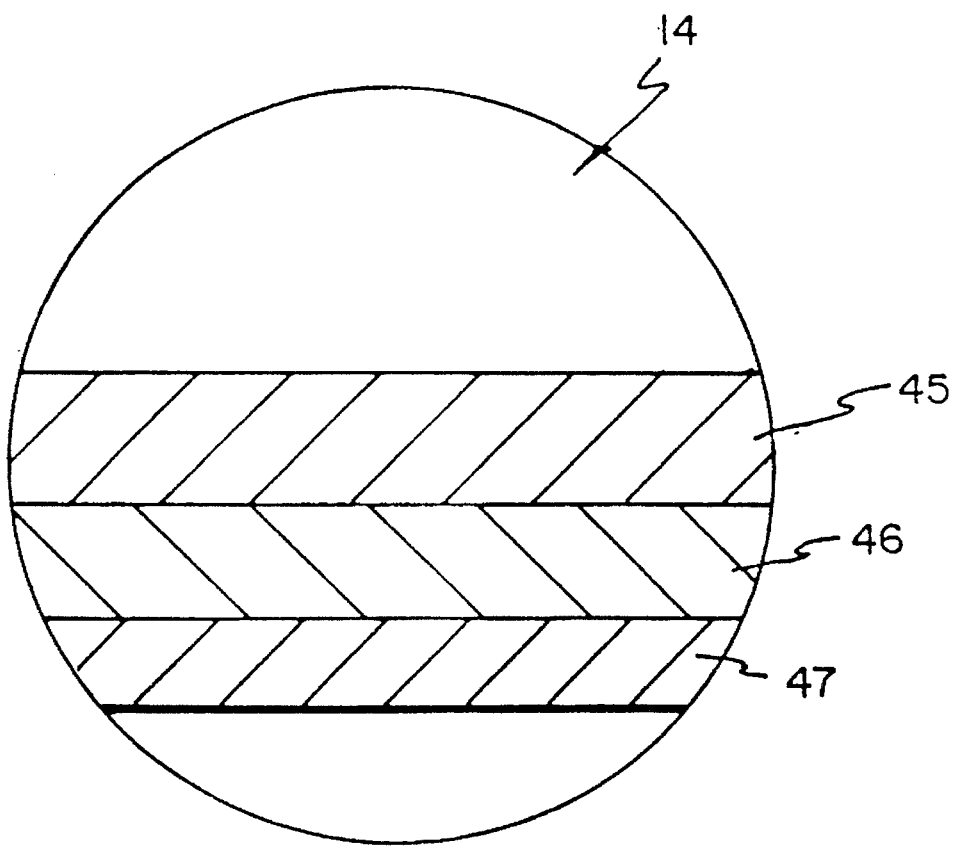
FIG. 4A is an enlarged cross-sectional view of a portion of the wall of a balloon of the present invention, having an outer layer of antifriction material thereon.
FIG. 4B is an enlarged cross-sectional view of a portion of the wall of a balloon of the present invention, having a plurality of layers of material defining that wall.
Figure 4A:
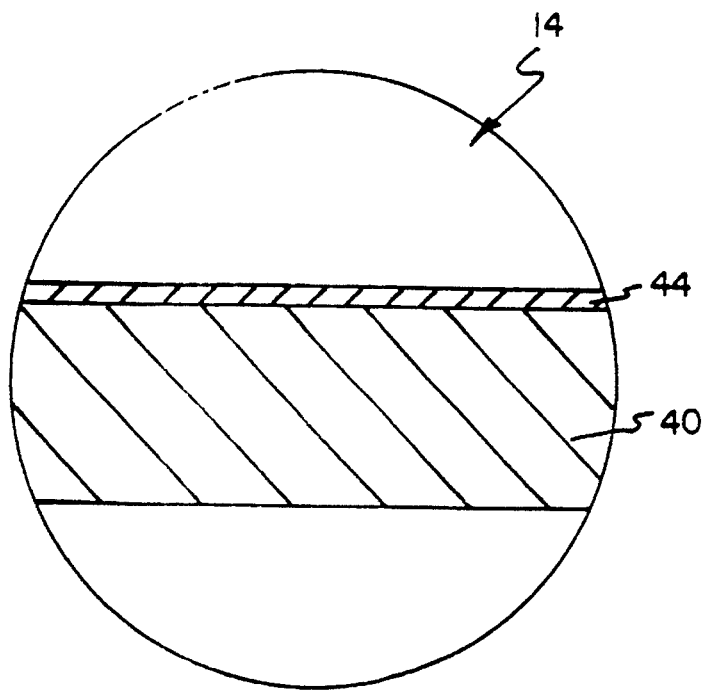

Other advantageous features can be obtained using other embodiments of the present invention. For example, as illustrated in FIG. 4A, layers of different materials can be deposited to form the balloon 14. In one embodiment, an antifriction coating is deposited as a final outer layer of the balloon. A suitable coating material (which provides antifriction characteristics without significantly increasing wall thickness) is Paralene C, with a thickness of about 1500A or less.

Figure 4B:
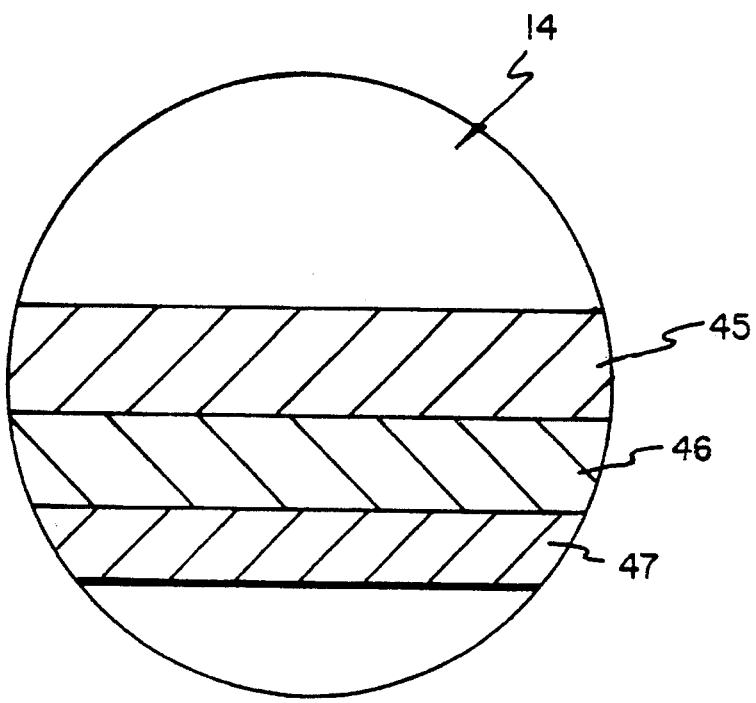

In another embodiment, a thin metal layer (e.g. layer 45 in FIG. 4B) is deposited between polymer layers (e.g. layers 45 and 47 in FIG. 4B) or as an inner layer or outer layer (layer 47). This offers a capability of applying localized heat at the stenosis during inflation by directing RF energy (or another form of electrical or electromagnetic energy) to the metal layer.

In still another embodiment, a colorant is added to one or more layers deposited to form the balloon. The colorant is capable of absorbing energy (e.g. radiation from a laser beam directed through the catheter to the balloon) for applying localized heat.

In the preferred embodiment of the method of the present invention described in FIGS. 2A–2C, substrate 30 has a surface configuration which corresponds to the desired shape of the balloon in a fully inflated condition. Conversely, the surface configuration of substrate 30 can correspond to the desired shape of the balloon in a deflated condition (or in a partially inflated condition). This latter embodiment is particularly advantageous for ensuring that the balloon has a minimum profile when deflated by making the shape of the deflated balloon predictable. By using this embodiment, creasing and heat setting characteristics may not be required. FIGS. 3A and 3B illustrate an example of this embodiment. FIG. 3A is a cross section of balloon 50 in a deflated condition, which has been defined by substrate 52 having three lobes 54A–54C. As a result, balloon 50 has three corresponding lobes 56A–56C when deflated. FIG. 3B shows the fully inflated state of balloon 50.

Other and alternative steps can be used with the present invention. For example, depending upon the particular material being deposited, a variety of different deposition techniques can be employed, including dip coating, vapor deposition, electroplating, and sputtering.

Similarly, although chemical removal of the substrate is preferred, other techniques are also possible. For example, when the substrate has a melting temperature which is lower than that of the deposited layer (or layers), the substrate can be removed by heating the substrate to its melting temperature.

Finally, when polyimide is used as the polymer material, the two stage process used to form the polyimide offers an opportunity to perform intermediate processing. When the layer is in the polyaminoacid state (i.e. prior to final cure), it is more amenable to mechanical forming such as stretching, necking and drawing/orientation steps. These steps are preferably performed prior to the final cure.

Although the present invention has been described with reference to preferred embodiments, workers skilled in the art will recognize that changes may be made in form and detail without departing from the spirit and scope of the invention.

What is claimed is:

1. A dilatation balloon catheter for applying pressure and heat to a stenosis within a patient's artery comprising:
   a shaft having an inflation lumen extending therethrough from a proximal end to a distal end; and
   a thin-walled inflatable balloon at the distal end of the shaft, the balloon being in fluid communication with the inflation lumen and being defined by a wall having a wall thickness of less than about 0.001 inches, a substantial portion of which is formed of polyimide polymer material, including an innermost polyimide layer defining an inner surface of the balloon, and an outer layer of an anti-friction material having a thickness of no greater than about 1,500 Angstroms, an intermediate metal film layer formed by deposition which heats in response to an application of electromagnetic energy thereto to apply heat radially outward to the stenosis while the balloon is inflated; wherein the balloon has a proximal section connected to the distal end of the shaft, an intermediate inflatable section, and a distal section.

2. The dilatation balloon catheter of claim 1 wherein the balloon has a wall thickness of about 0.0003 inches.

3. The dilatation balloon catheter of claim 1 wherein the balloon has strength and tear resistance properties which are determined by the layers of polyimide polymer material.

4. A dilatation balloon catheter for angioplasty, the catheter comprising:

an elongated flexible shaft having an inflation lumen extending from a proximal end to a distal end; and an inflatable balloon, a substantial portion of which is formed of polyimide, the balloon having a proximal section connected to the distal end of the shaft, an intermediate balloon section, and a distal section, the intermediate section having an outer diameter, when inflated, which is greater than the proximal section and the distal section, the balloon having a wall thickness of less than about 0.001 inches and having strength and tear resistance properties determined by the polyimide; and the balloon having a deposited metal film layer which heats in response to electromagnetic energy being applied thereto to apply heat radially outward to the stenosis while the balloon is inflated.

5. The dilatation balloon catheter of claim 4 and further comprising:

an outer layer of an anti-friction material over an outermost layer of polyimide.

6. The dilatation balloon catheter of claim 5 wherein the outer layer has a thickness of no greater than about 1,500 Angstroms.

7. The dilatation balloon catheter of claim 4 wherein the wall thickness is about 0.0003 inches.

8. A dilatation balloon catheter for applying pressure and heat to a stenosis within a patient's artery, the catheter comprising:

an elongated flexible shaft having an inflation lumen extending from a proximal end to a distal end; and an inflatable balloon having a wall thickness of about 0.0003 inches, wherein a portion of the balloon is formed of a polymeric material and including a thin continuous and gapless coating defining at least one entire contour of the inflatable balloon and consisting solely of metal formed by deposition upon an outer surface of the polymeric material, wherein the coating has a length, a width and a thickness, wherein the thickness is substantially uniform throughout the coating, wherein the length is larger than the width, and wherein the width is at least twice as large as the thickness, wherein the coating heats in response to electromagnetic energy being applied thereto.

9. The dilatation balloon catheter of claim 8 and further comprising:

a layer of an anti-friction material over the portion formed of a polymeric material.

10. The dilatation balloon catheter of claim 9 wherein the layer of anti-friction material has a thickness of no greater than about 1,500 Angstroms.

11. The dilatation balloon catheter of claim 8 wherein the balloon has a wall thickness of about 0.0003 inches.

12. The balloon dilatation catheter of claim 8 wherein the deposited thin coating has a uniform thickness throughout the contour of the balloon.

13. A balloon dilatation catheter for applying heat to a stenosis within a patient's artery during dilatation of the stenosis, the balloon dilatation catheter comprising:

an elongated shaft having an inflation lumen extending between a proximal end and a distal end; and a multilayer inflatable balloon at the distal end of the shaft and having an interior in communication with the inflation lumen, the balloon including at least a portion of which comprises a polymeric layer and a deposited thin continuous and gapless coating upon an outer surface of the polymeric layer, wherein the coating defines at least one entire contour of the inflatable balloon and consists solely of metal which heats in response to electromagnetic energy being applied thereto, the deposited thin coating being positioned for receiving the electromagnetic energy and applying localized heat radially outward to the stenosis while the balloon is inflated.

14. The balloon dilatation catheter of claim 13 wherein the balloon has a wall thickness of less than 0.001 inches.

15. The balloon dilatation catheter of claim 13 wherein the balloon includes a plurality of polymeric layers and the deposited thin coating is located between polymeric layers.

16. The balloon dilatation catheter of claim 13 wherein the deposited coating has a uniform thickness throughout the contour of the balloon.

17. A dilatation balloon catheter for applying pressure and heat to a stenosis within a patient's artery, the catheter comprising:

an elongated flexible shaft having an inflation lumen extending from a proximal end to a distal end; and an inflatable balloon, a substantial portion of which is formed by a polymeric material and including a thin continuous and gapless metal coating formed by deposition upon an outer surface of the polymeric material, wherein the metal coating defines at least one entire contour of the inflatable balloon and wherein the metal coating heats in response to electromagnetic energy being applied thereto, the deposited thin metal layer being positioned for receiving the electromagnetic energy and applying localized heat radially outward to the stenosis while the balloon is inflated.

18. A method for forming a thin walled inflatable balloon for use in a dilatation balloon catheter, the method comprising the steps of:

providing a substrate having an exterior surface configuration which corresponds to a desired shape of the balloon in a predetermined condition;

depositing a first liquid coating over the entire exterior surface of the substrate, wherein the first liquid coating has an exterior surface corresponding to the desired shape of the balloon;

drying the first liquid coating;

depositing a second liquid coating over the entire exterior surface of the first dried liquid coating, wherein one of the coatings is a metallic material which heats in response to an application of electromagnetic energy thereto; and removing the substrate within the coatings to leave a balloon of the desired shape.

19. The method of claim 18 wherein the first and second coatings are deposited by dip coating the substrate.

20. A dilatation balloon catheter for applying pressure and heat to a stenosis within a patient's artery, the catheter comprising:

an elongated flexible shaft having an inflation lumen extending from a proximal end to a distal end; and an inflatable balloon having a wall thickness of about 0.0003 inches, wherein a portion of the balloon is formed of a polymeric material and including a thin continuous and gapless coating consisting solely of metal formed by deposition upon an outer surface of the polymeric material, wherein the coating heats in response to electromagnetic energy being applied thereto.

21. The dilatation balloon catheter of claim 20 and further comprising:

a layer of an anti-friction material over the portion formed of a polymeric material.

22. The dilatation balloon catheter of claim 21 wherein the layer of anti-friction material has a thickness of no greater than about 1,500 Angstroms.

* * * * *

UNITED STATES PATENT AND TRADEMARK OFFICE
CERTIFICATE OF CORRECTION

PATENT NO. : 5,499,980
DATED : March 19, 1996
INVENTOR(S) : CHARLES L. EUTENEUER It is certified that error appears in the above-indentified patent and that said Letters Patent is hereby corrected as shown below:

On the title page, item [56] under "References Cited", insert

--4,487,808    12/1984    Lambert       606/108--
--4,786,556    11/1988    Hu et al.     515/822--
--4,884,573    12/1989    Wijay et al.  606/194--

Col. 4, line 4, delete "45", insert --46--

Col. 4, line 6, after "inner", delete "layer"

Col. 4, line 7, delete "(layer 47)"

Col. 4, line 30, before "balloon", delete "," (second occurrence)

Signed and Sealed this

Thirtieth Day of July, 1996

Attest:

BRUCE LEHMAN

*Attesting Officer*     Commissioner of Patents and Trademarks